US012364712B2

(12) United States Patent
Olson

(10) Patent No.: US 12,364,712 B2
(45) Date of Patent: Jul. 22, 2025

(54) MINERAL SUPPLEMENTS FOR RUMINANT NUTRITION

(71) Applicant: ALBERTA VETERINARY LABORATORIES LTD., Calgary (CA)

(72) Inventor: Merle Olson, Calgary (CA)

(73) Assignee: ALBERTA VETERINARY LABORATORIES LTD., Calgary (CA)

( * ) Notice: Subject to any disclaimer, the term of this patent is extended or adjusted under 35 U.S.C. 154(b) by 0 days.

(21) Appl. No.: 17/784,575

(22) PCT Filed: Dec. 11, 2020

(86) PCT No.: PCT/CA2020/051708
§ 371 (c)(1),
(2) Date: Jun. 10, 2022

(87) PCT Pub. No.: WO2021/113982
PCT Pub. Date: Jun. 17, 2021

(65) Prior Publication Data
US 2023/0014993 A1    Jan. 19, 2023

Related U.S. Application Data

(60) Provisional application No. 62/947,329, filed on Dec. 12, 2019.

(51) Int. Cl.
*A61K 33/42* (2006.01)
*A23K 20/174* (2016.01)
*A23K 50/10* (2016.01)
*A61K 47/14* (2017.01)
*A61K 47/38* (2006.01)

(52) U.S. Cl.
CPC ............ *A61K 33/42* (2013.01); *A23K 20/174* (2016.05); *A23K 50/10* (2016.05); *A61K 47/14* (2013.01); *A61K 47/38* (2013.01)

(58) Field of Classification Search
CPC ........ A61K 33/42; A61K 47/14; A61K 47/38; A61K 9/0068; A23K 20/174; A23K 50/10; A23K 20/158; A23K 20/163; A23K 20/24; A23K 20/26; A23K 20/22; A23K 20/30; A23K 40/35; A61P 3/12
See application file for complete search history.

(56) References Cited

U.S. PATENT DOCUMENTS

| 4,867,977 A | 9/1989 | Gailly et al. |
| 5,093,128 A | 3/1992 | Draguesku et al. |
| 5,807,594 A | 9/1998 | King et al. |
| 6,355,281 B1 | 3/2002 | Cerchiari et al. |
| 2007/0098810 A1 | 5/2007 | Lee |
| 2011/0189132 A1* | 8/2011 | Garner .................. A61K 45/06 424/93.3 |
| 2014/0057022 A1 | 2/2014 | Hoejvang-Nielsen |

FOREIGN PATENT DOCUMENTS

WO    9608168 A1    3/1996

OTHER PUBLICATIONS

International Search Report and Written Opinion mailed Mar. 4, 2021.
Wittek, et al., "Comarative study on 3 oral potassium formulations for treatment of hypokalemia in dairy cows", J. Vet Intern. Med., May 6, 2019.
Extended European Search Report based on Application No. 20899993.8; mailed on Dec. 22, 2023. 11 pages.
Cohrs, Imke , et al., "Suitability of oral administration of monosodium phosphate, disodium phosphate, and magnesium phosphate for the rapid correction of hypophosphatemia in cattle", Journal of veterinary internal medicine 32.3 (2018): 1253-1258.
Jayaprakash, G. , et al., "Rumen-protected choline: A significance effect on dairy cattle nutrition", Veterinary World, EISSN: 2231-0916, www.veterinaryworld.org/Vol.9/August-2016/7.pdf, 837-841.
Pineda, A. , et al., ""Effects of rumen-protected choline with calcium salts of long chain fatty acids on milk yield and milk composition of middle and late lactation Holstein cows"", Livestock Science 175 (2015) 47-58, Department of Animal Sciences, http://dx.doi.org/10.1016/j.livsci.2015.02.005.
Seyama, Tomohiro , et al., "Development of three-layered rumen escapable capsules for cattle", Journal of Veterinary Medical Science 78.12 (2016): 1765-1769.

* cited by examiner

Primary Examiner — Jessica Worsham
(74) Attorney, Agent, or Firm — Billion & Armitage

(57) ABSTRACT

Disclosed are bolus compositions for ruminants comprising potassium phosphate dibasic and water configured to rapidly dissolve in the rumen for use in the prevention or treatment of hypokalemia and hypophosphatemia. These conditions occur in ruminants at around the time of calving or during periods when ruminants do not eat (anorexia). The bolus compositions may comprise a coating that is compatible with a ruminant digestive tract. Additionally, the bolus compositions may comprise a wick which may be used during the manufacturing process to facilitate the bulk handling and transfer of the bolus compositions.

13 Claims, 4 Drawing Sheets

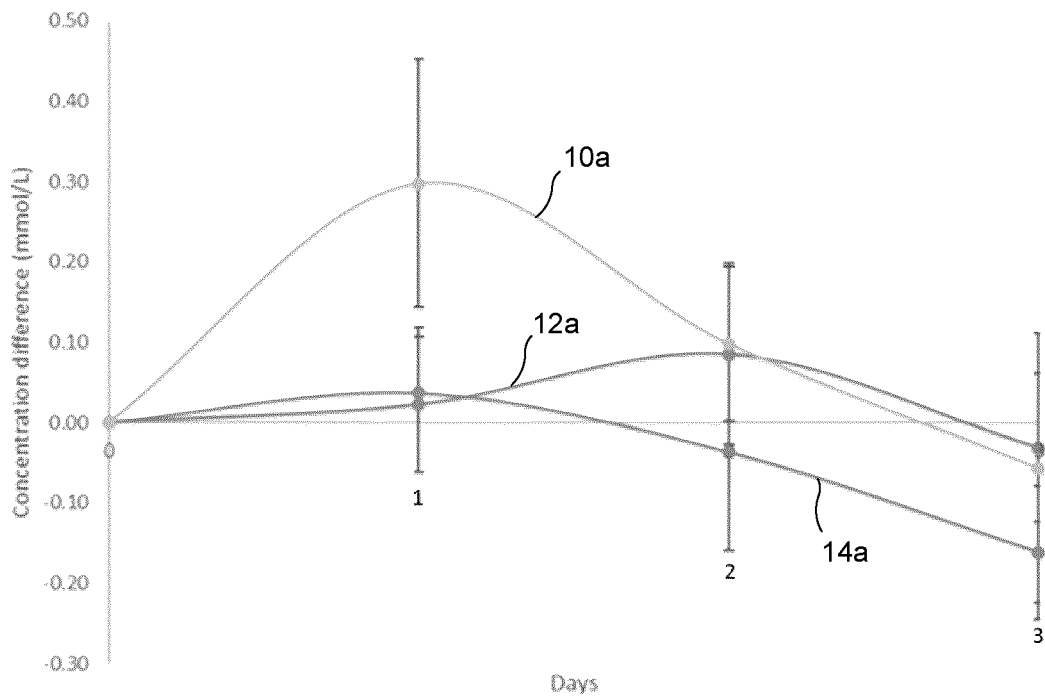
FIG. 2A
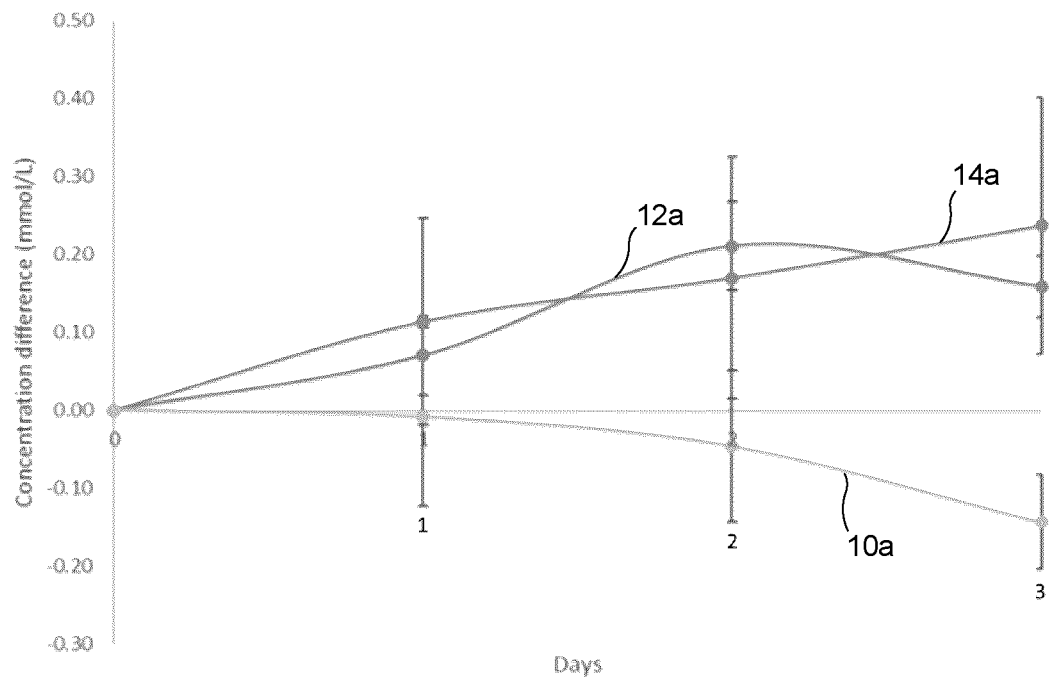
FIG. 2B
FIG. 2

MINERAL SUPPLEMENTS FOR RUMINANT NUTRITION

This application is a National Stage Application of PCT/CA2020/051708, filed 11 Dec. 2020, which claims benefit of Application No. 62/947,329, filed 12 Dec. 2019 in the US and which applications are incorporated herein by reference. A claim of priority to all, to the extent appropriate, is made.

TECHNICAL FIELD

This disclosure generally relates to bolus compositions comprising mineral nutrients for ruminants. More specifically, this disclosure pertains to bolus compositions for rapid delivery of selected nutrients to ruminants in physiological distress due to nutrient deficiencies.

BACKGROUND

The process of calving is both physically and physiologically taxing on ruminants such as bovines. In terms of physiological stresses, pregnancy, calving, and the onset of lactation can result in variety of nutritional deficiencies. These deficiencies may then in turn, physiologically debilitate the mother. As well, if such deficiencies are not prophylactically managed, or alternatively, appropriately treated as necessary during the course of the pregnancy, they may also affect the well-being of the calf.

For example, common nutritional deficiencies arising during pregnancy and calving include mineral and vitamin deficiencies in, for example, calcium, phosphorous, selenium, potassium, sodium, and chloride as well as the vitamins A, D, and E. These deficiencies may lead to a variety of physiological and physical issues in the mother or calf such as milk fever, muscle weakness, recumbency, and the like.

Of these deficiencies, hypophosphatemia (low phosphorous levels in blood or tissue) and hypokalemia (low potassium levels in blood or tissue) are particularly problematic. Both conditions may occur in ruminants at around the time of calving, and also during periods when ruminants do not eat (anorexia). Hypophosphatemia and hypokalemia have similar symptoms including muscle weakness, ataxia, and recumbency. As well, if the deficiencies are not promptly or adequately treated, they may result in the death of the afflicted ruminant.

Diagnosis of hypophosphatemia may be difficult as a laboratory analysis of a blood sample collected from the potentially afflicted ruminant is required, which takes time to process and can be expensive. Hypokalemia diagnosis on the other hand, may be difficult because potassium is primarily an intracellular ion and, as a result, low potassium levels in ruminant blood only occur when the animal is near death.

Presently, treatment of hypophosphatemia and hypokalemia is also difficult and has significant risks. Specifically, current treatments require administration of sodium phosphate or potassium chloride by way of drenching the afflicted ruminants. Drenching involves passing a tube down the throat of the ruminant and pumping a solution of the sodium phosphate or potassium chloride thereinto its rumen. This operation is difficult, as the animal must be restrained while simultaneously taking care not to pump the salt solution into the lungs of the animal, which may be fatal.

SUMMARY

Embodiments of the present disclosure generally relate to bolus compositions for use in the prevention or treatment of nutrient deficiencies in ruminants. More specifically, the bolus compositions are for use to prevent or treat hypophosphatemia and hypokalemia. The bolus compositions comprise a mixture of potassium phosphate dibasic and water, and are configured to rapidly dissolve in the rumen of a ruminant thereby rapidly providing supplemental potassium and phosphorus to the animal. The bolus compositions may be administered either prior to anticipated nutritional deficiencies such as those relating to calving in order to prevent such deficiencies, or alternatively may be administered to treat a nutritionally deficient ruminant.

Thus, one aspect of the present disclosure relates to bolus compositions for use to prevent or treat hypokalemia and hypophosphatemia in a ruminant. The bolus compositions may comprise about 70 wt % to about 80 wt % potassium phosphate dibasic and about 20 wt % to about 30 wt % water.

Another aspect of the present disclosure relates to use of the bolus compositions described herein for the prevention or treatment of hypophosphatemia and/or hypokalemia in a ruminant.

Yet another aspect of the present disclosure relates to a method of preventing or treating hypophosphatemia and/or hypokalemia in a ruminant, the method comprising administering at least one of the bolus compositions described herein to the ruminant.

BRIEF DESCRIPTION OF THE FIGURES

The embodiments of the present disclosure will be described with reference to the following drawings in which:

FIG. 2 includes a first chart FIG. 2A, which shows the mean change in blood serum phosphate, magnesium, and calcium levels in dairy cattle treated with bolus compositions of the present disclosure as compared to levels before treatment, and a second chart FIG. 2B, which shows the mean change in blood serum phosphate, magnesium, and calcium levels in dairy cattle not treated with bolus compositions of the present disclosure as compared to levels before treatment;

DETAILED DESCRIPTION

Figure 1:
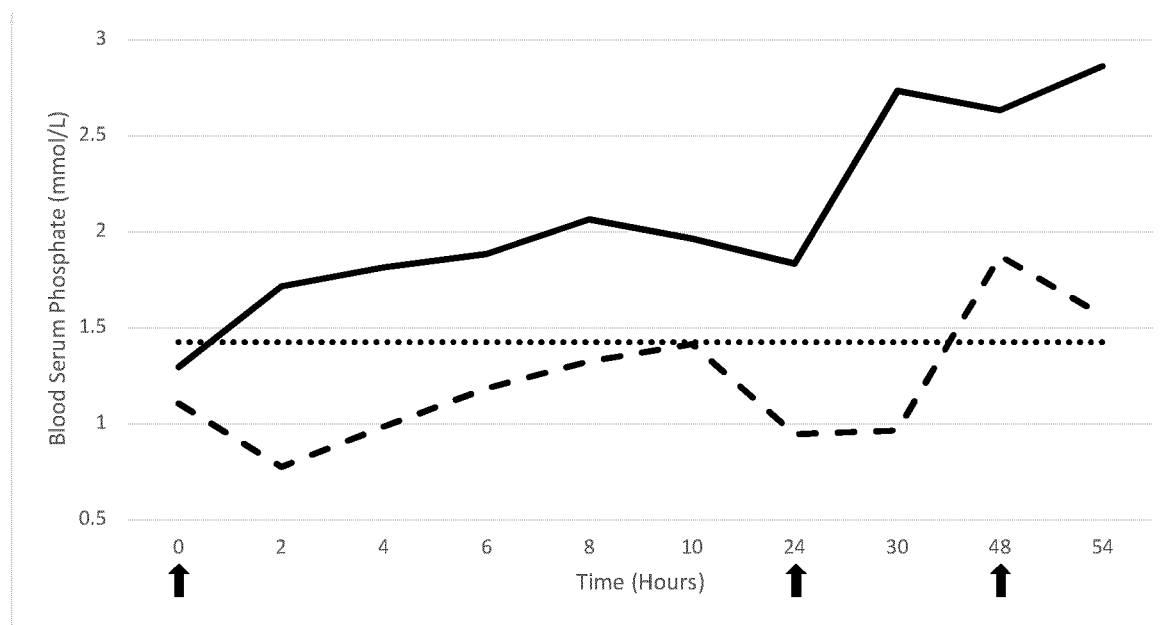
FIG. 1 is a chart showing the mean change in blood serum phosphate levels in dairy cattle that were treated with the bolus compositions of the present disclosure and that were not treated with the bolus compositions over time.

The embodiments of the present disclosure generally relate to bolus compositions for use to prevent or treat nutrient deficiencies in ruminants. The bolus compositions may be easily delivered into the digestive tract of deficient ruminants in order to rapidly supply nutrients thereto.

The bolus compositions of the present disclosure may provide a number of advantages. For example, and as will be discussed in greater detail below, the bolus compositions of the present disclosure comprise a potassium phosphate salt in such an amount that the bolus compositions are capable of simultaneously treating both hypophosphatemia and hypokalemia in ruminants.

Further, the bolus compositions of the present disclosure are solid, which means that the potassium phosphate salt may be administered to the ruminants in a manner other than drenching. As will be appreciated, this avoids the risk of a salt solution entering the lungs of the ruminants, which may be uncomfortable and, in some cases, fatal.

Furthermore, the bolus compositions of the present disclosure may be capable of treating diseases associated with hypophosphatemia and hypokalemia. For example, hypophosphatemia and hypokalemia are often accompanied by anorexia. Anorexia, as will be appreciated, may lead to hypophosphatemia, which in turn, may lead to anorexia. Thus, the ruminants may enter a cycle of anorexia and hypophosphatemia. The bolus compositions of the present disclosure, however, may act to break the cycle by treating the hypophosphatemia which then motivates the animals to eat, thereby also addressing the anorexia.

The bolus compositions may also be used to help ranchers and producers with feedlot management. In more detail, if ruminants in feedlots do not eat, they are moved to sick pens wherein, if they fail to eat or gain weight, they are euthanized. It has been found that ruminants in the sick pens of feed lots are often hypophosphatemic. In fact, in some cases, about 50% to about 55% of the animals in the sick pens are hypophosphatemic. As well, calves may be stressed when first delivered to feed lots. It has also been found that about 50% to about 55% of stressed calves are hypophosphatemic. Thus, the bolus compositions of the present disclosure may advantageously be administered to the animals upon their arrival at the feedlot to thereby reduce the need to send animals to sick pens and/or to reduce the side effects caused by stress.

Furthermore, the bolus compositions may be easily manufactured as they may require minimal amounts of components to produce. As a result, manufacturing of the bolus compositions may be readily up-scaled to industrially relevant levels.

As used herein, the term "ruminant" is intended to encompass any animal that obtains nutrients by fermenting plant-based foods in a rumen prior to digestion. For example, such animals include bovines, goats, sheep, and deer. Further, as used herein, the term "bovine" is intended to encompass cattle such as beef or dairy cows, bison, and buffalo.

As indicated above, ruminants have a unique digestive tract in which food is fermented prior to digestion. Specifically, and as used herein, the "ruminant digestive tract" includes an esophagus, a stomach having a rumen, a reticulum, an omasum, and an abomasum, which then connects to a small intestine and then further to a large intestine. As will be understood by a person of ordinary skill in the art, the rumen acts as the primary site of microbial fermentation in the ruminant digestive tract.

As used herein, the term "bolus" refers to solid compositions for delivery to the rumen of a ruminant. The bolus may have a shape that facilities easy swallowing by a ruminant. For example, the bolus may be generally spherical, cylindrical, capsular, torpedo-shaped, or donut-shaped. As well, the bolus may have at least one rounded end. The rounded end may reduce irritation of the esophagus of the ruminant by removing or softening a leading edge of the bolus. Advantageously, the bolus may be administered to the rumen of a ruminant with relative ease. For example, the bolus may be administered using a balling gun. As will be appreciated by a person of ordinary skill in the art, such administration is considerably easier than, for example, drenching, as the animal does not need to be as heavily restrained, and there is no risk of a salt solution entering the lungs of the animal.

More specifically, an aspect of the present disclosure relates to bolus compositions for use to prevent and treat of hypokalemia and hypophosphatemia in ruminants. The bolus compositions comprise a mixture of potassium phosphate dibasic and water. The use of potassium phosphate dibasic advantageously allows for the simultaneous prevention or treatment of hypophosphatemia or hypokalemia. The bolus, once delivered to the ruminant digestive tract, rapidly dissolves in the rumen to release and provide potassium and phosphorus. The potassium and phosphorous provided by the bolus are then absorbed into the blood and tissues of the animal.

According to an embodiment, the bolus compositions of the present disclosure comprise about 70 wt % to about 80 wt % potassium phosphate dibasic and about 20 wt % to about 30 wt % water. According to one aspect, the weight ratio of potassium phosphate dibasic to water is 80:20. In some embodiments, the bolus compositions may also comprise additional vitamins and/or minerals to facilitate and maintain the physiological and physical health of ruminants. Example vitamins and/or minerals include without limitation one or more of calcium, selenium, sodium, zinc, iodine, chloride, copper, and choline as well as vitamins A, D, and E.

According to a further embodiment, the bolus compositions may have a weight of about 50 g to about 250 g. In such an embodiment, the bolus compositions may have a diameter of about 1 cm to about 3.5 cm and a length of about 3 cm to about 20 cm. As will be appreciated, the size and weight of the bolus compositions may be adjusted based on the ruminant to which the bolus is to be administered. For example, a bolus composition prepared for administration to an adult bovine may be larger than those prepared for administration to calves, sheep, or goats. According to an aspect, a bolus composition for administration to an adult bovine may have a weight of about 150 g to about 300 g, whereas a bolus composition for administration to calves, sheep, or goats may have a weight of about 40 g to about 100 g. Advantageously, due to the solubility of the potassium phosphate dibasic and, if present, the use of a compatible coating, the bolus compositions are capable of dissolving in a rumen in about 10 min to about 20 min, even at the larger sizes and weights such as 250 g. The bolus compositions are therefore capable of rapidly delivering a relatively high dosage of potassium and phosphorous to the rumen of a ruminant. Notably, the content of potassium and phosphorous delivered may be sufficient to elevate and maintain the levels thereof in a ruminant for about 12 h to about 24 h. However, it may also be desirable to administer the bolus compositions 2 times or 3 times per day over the course of 1 day to 5 days, based on the preventative measures or treatment required.

According to another embodiment, the bolus compositions of the present disclosure may also comprise a coating that is compatible with a ruminant digestive tract. That is, the coating may be any substance that allows for rapid dissolution in the rumen while also being non-irritating to the esophagus of the ruminant, which is particularly useful if repeat administrations of bolus compositions are required. According to an aspect, the coating may be a lipid-based coating. According to another aspect, the coating may comprise an acetylated triglyceride. The coating may be provided in any amount that sufficiently coats the bolus composition. According to an aspect, the coating may be present in an amount of about 1 g to about 10 g.

According to a further embodiment, the bolus compositions of the present disclosure may comprise a wick. The wick may be used during the manufacturing process to facilitate the bulk handling and transfer of the bolus compositions described herein. According to one aspect, the wick may be a biodegradable wick. As used herein, "biodegradable wick" refers to a wick that will degrade, dissolve, or decompose in the digestive tract of a ruminant. According to another aspect, the biodegradable wick may be formed of cellulose or a cellulosic material. According to a further aspect, the wick may be a removable wick. In such an aspect, the wick is used during the production of the bolus composition, but may be removed prior to administration to the ruminant. In aspects where the wick is removable, it may be made of a material that does not degrade, dissolve, or decompose in the digestive tract of the ruminant.

As will become apparent from the examples disclosed herein, the bolus compositions of the present disclosure may advantageously be manufactured with relative ease, due to the chemical properties of the potassium phosphate dibasic. Specifically, the solubility of potassium phosphate dibasic allows for a relatively large amount of the salt to be dissolved in a relatively small amount of water (e.g. at a salt to water ratio of 80:20). Potassium phosphate dibasic is also hygroscopic and will rapidly absorb the water into which it has been dissolved such that, if left to set, a solid mass forms. As well, because the dissolution is an exothermic reaction, an external heat source is not required to facilitate the reaction, thereby simplifying the process.

EXAMPLES

Example 1: Preparation of a Bolus Composition Using Potassium Phosphate Dibasic

A bolus composition comprising about 80 wt % potassium phosphate dibasic and about 20 wt % water was produced using the procedure outlined below.

About 6 kg of potassium phosphate dibasic were added to about 1.5 kg of water in a mixing vessel in order to form a salt-water solution. The salt-water solution was mixed until the salt fully dissolved. The dissolution of the potassium phosphate dibasic is an exothermic reaction and thereby heated the salt-water solution during the mixing process.

The heated salt-water solution was then poured into an aluminum mold having a cylindrical shape with a rounded bottom, a diameter of about 1.26 in (3.24 cm), and a length of about 6 in (15.2 cm). Immediately thereafter, a cellulose wick of about 2 in (5.08 cm) in length was inserted into the salt-water solution to a depth of about 1 in (2.54 cm). The salt-water solution was then allowed to set in the mold for about 12 h, during which time the solution cooled to room temperature and solidified to form the present bolus compositions, each having a weight of about 209 g.

The solidified bolus compositions were then removed from the aluminum molds and then dipped into a molten acetylated triglycerides solution at about 50° C. The dipping of the uncoated bolus compositions was done by gripping the wicks extending therefrom and submerging each uncoated bolus composition entirely into the acetylated triglycerides solution. The bolus compositions, again using the wick, were then removed from the acetylated triglycerides solution and the coatings were allowed to dry. Each dried coated bolus composition had a weight of about 215 g.

It is noted that the bolus composition may be made without the use of a wick. For example, the application of the coating may be completed by dipping half of the uncoated bolus composition into the acetylated triglycerides solution and allowing the coating to dry, and subsequently dipping the remaining uncoated half of the bolus composition into the acetylated triglycerides solution and again allowing the coating to dry.

Example 2: Bolus Composition In Vitro Dissolution Test

A bolus composition manufactured as described in Example 1 was tested to evaluate its dissolvability in the rumen of ruminants. The experiment was conducted using a fistulated Jersey steer aged about 28 months and about 12 months post-cannulation.

The bolus composition of the present disclosure was weighed, placed in a mesh netting, and positioned in the rumen of the cow via its cannula along with a pH probe, provided by Dascor (Oceanside, California, US). The bolus composition was removed using the netting from the cow 30 min, 60 min, 90 min, 120 min, 180 min, and 240 min after insertion or until the bolus composition had completely dissolved, weighed, and returned to the rumen. Each time the bolus composition was removed, a sample of fluid was taken from the lower level of the rumen and tested with a pH strip provided by VWR Chemicals BDH (Radnor, Pennsylvania, US). The results of the tests are shown below in Table 1.

TABLE 1

| Change in bolus composition weight over time in cattle rumen | | | |
|---|---|---|---|
| Time (min) | Bolus Weight (g) | Percent Remaining of Bolus | Rumen pH |
| 0 | 223 | 100% | 7.5 |
| 30 | 153 | 69% | 7.5 |
| 60 | 91 | 41% | 7.5 |
| 90 | 0 | 0% | 7.5 |

Thus, the bolus composition completely dissolved in the rumen of the cow in about 90 mins and without affecting the pH of its rumen, thereby confirming the ability of the bolus compositions of the present disclosure to rapidly deliver potassium and phosphorus to a ruminant.

Example 3: Treatment of Hypophosphatemia in Post-Partum Dairy Cattle Using Bolus Compositions of the Present Disclosure Bolus compositions manufactured in the manner described in Example 1 were used to evaluate their effects in calving dairy cows having a parity of 3 or greater.

The experiment was conducted using 8 cattle; 5 test animals and 3 control animals. Two bolus compositions were administered to each of the 5 test animals at calving, 0 to 12 hours after the first administration, 24 hours after the first administration, and 48 hours after the first administration. The 3 control animals were not administered bolus compositions.

Blood samples were taken from the all of the cattle before the first administration of the bolus compositions the test animals (time 0), 2 hours after the first administration, 4 hours after the first administration, 6 hours after the first administration, 8 hours after the first administration, 10 hours after the first administration, 24 hours after the first administration, 30 hours after the first administration, 48 hours after the first administration, and 54 hours after the first administration. The blood samples were collected in red-top tubes and centrifuged to extract serum therefrom.

Phosphate, calcium, and magnesium levels of the extracted blood serum samples were then measured using phosphate, calcium, and magnesium assay kits provided by BioAssay Systems (Hayward, CA, USA).

The results of the tests are outlined in the tables below. It is noted that Animal 1 had different blood sampling times than Animals 2 to 8, as will be indicated below.

TABLE 2

Concentration of phosphate in dairy cow blood serum samples

| Time (Hr) | Animal 1 Test Conc (mmol/L) | Time (Hr) | Animal 2 Control Conc (mmol/L) | Animal 3 Test Conc (mmol/L) | Animal 4 Control Conc (mmol/L) | Animal 5 Test Conc (mmol/L) | Animal 6 Test Conc (mmol/L) | Animal 7 Test Conc (mmol/L) | Animal 8 Control Conc (mmol/L) |
|---|---|---|---|---|---|---|---|---|---|
| 0 | 1.65 | 0 | 0.89 | 1.58 | 1.59 | 1.07 | 1.07 | 1.08 | 0.81 |
| 2 | 1.97 | 2 | 0.70 | 1.98 | No sample | 1.46 | 1.71 | 1.43 | 0.85 |
| 4 | 2.11 | 4 | 0.71 | 2.43 | 1.32 | 1.53 | 1.50 | 1.48 | 0.91 |
| 6 | 2.39 | 6 | 1.20 | 2.57 | 1.19 | 1.29 | 1.64 | 1.52 | 1.15 |
| 8 | 2.69 | 8 | 1.45 | 2.45 | 1.36 | 1.52 | 1.92 | 1.75 | 1.15 |
| 10 | 2.60 | 10 | 1.76 | 2.49 | 1.00 | 1.11 | 2.11 | 1.48 | 1.47 |
| 12 | | 24 | 1.19 | 2.16 | 0.77 | 1.08 | 2.62 | 1.46 | 0.88 |
| 14 | | 30 | 0.91 | 2.19 | No sample | No sample | 2.63 | 3.37 | 1.02 |
| 16 | | 48 | 1.19 | 2.15 | 2.53 | 2.41 | 2.77 | 3.18 | 1.90 |
| 18 | | 54 | 1.11 | 2.46 | No sample | 2.83 | 2.51 | 3.66 | 2.02 |

TABLE 3

Concentration of calcium in dairy cow blood serum samples

| Time (Hr) | Animal 1 Test Conc (mmol/L) | Time (Hr) | Animal 2 Control Conc (mmol/L) | Animal 3 Test Conc (mmol/L) | Animal 4 Control Conc (mmol/L) | Animal 5 Test Conc (mmol/L) | Animal 6 Test Conc (mmol/L) | Animal 7 Test Conc (mmol/L) | Animal 8 Control Conc (mmol/L) |
|---|---|---|---|---|---|---|---|---|---|
| 0 | 6.78 | 0 | 7.76 | 7.75 | 9.17 | 9.41 | 7.34 | 9.41 | 5.84 |
| 2 | 7.58 | 2 | 9.02 | 7.98 | 6.69 | 10.57 | 7.68 | 8.37 | 5.86 |
| 4 | 6.90 | 4 | 8.39 | 7.36 | No Sample | 10.58 | 5.73 | 7.30 | 6.70 |
| 6 | 6.84 | 6 | 10.22 | 7.37 | 5.92 | 7.88 | 8.32 | 5.93 | 7.19 |
| 8 | 6.65 | 8 | 10.05 | 7.73 | 6.63 | 9.02 | 7.46 | 6.90 | 6.29 |
| 10 | 6.16 | 10 | 9.81 | 8.63 | 7.58 | 11.60 | 7.58 | 7.08 | 7.66 |
| 12 | | 24 | 8.98 | 9.10 | 6.31 | No Sample | 5.95 | 7.09 | 7.88 |
| 14 | | 30 | 9.02 | 7.33 | No Sample | No Sample | 5.97 | 8.51 | 7.05 |
| 16 | | 48 | 7.66 | 9.77 | 9.42 | 11.02 | 7.47 | 7.32 | 8.90 |
| 18 | | 54 | 9.33 | 7.86 | No Sample | 8.83 | 10.10 | 8.24 | 7.50 |

TABLE 4

Concentration of magnesium in dairy cattle blood serum samples

| Time (Hr) | Animal 1 Test Conc (mmol/L) | Time (Hr) | Animal 2 Control Conc (mmol/L) | Animal 3 Test Conc (mmol/L) | Animal 4 Control Conc (mmol/L) | Animal 5 Test Conc (mmol/L) | Animal 6 Test Conc (mmol/L) | Animal 7 Test Conc (mmol/L) | Animal 8 Control Conc (mmol/L) |
|---|---|---|---|---|---|---|---|---|---|
| 2.88 | 0 | 2.32 | 2.11 | 5.40 | 2.35 | 2.94 | 2.71 | 3.47 | 2.88 |
| 3.10 | 2 | | 3.19 | 2.23 | 2.09 | 2.44 | 2.27 | 2.62 | 3.10 |
| 2.62 | 4 | 3.24 | No Sample | No Sample | No Sample | 2.18 | 2.74 | 2.51 | 2.62 |
| 2.44 | 6 | 2.62 | No Sample | 2.67 | No Sample | 2.25 | 3.10 | 3.01 | 2.44 |
| 4.97 | 8 | 3.26 | 1.43 | 2.90 | 2.34 | No Sample | No Sample | 2.94 | 4.97 |
| 3.45 | 10 | 2.11 | 1.35 | 2.55 | 3.47 | 2.69 | No Sample | 2.11 | 3.45 |
| | 24 | 3.33 | No Sample | No Sample | 2.69 | No Sample | 2.74 | 2.60 | No Sample |
| | 30 | 3.13 | 1.81 | No Sample | No Sample | 2.81 | 2.78 | 2.23 | No Sample |
| | 48 | 2.58 | 2.07 | No Sample | 2.41 | 2.16 | 2.37 | 2.96 | No Sample |
| | 54 | 2.74 | 2.11 | No Sample | 3.04 | 2.19 | 2.67 | 3.12 | No Sample |

Using the date outlined above in Tables 2 to 4, mean phosphate, magnesium, and calcium concentrations in blood serum samples extracted from the test and control animals were calculated, the results of which are outlined below.

TABLE 5

Mean concentration of phosphate in dairy cow blood serum samples

| Time (hrs) | Test Animals (n = 5) | Control Animals (n = 3) |
| --- | --- | --- |
| 0 | 1.29 | 1.10 |
| 2 | 1.71 | 0.77 |
| 4 | 1.81 | 0.98 |
| 6 | 1.88 | 1.18 |
| 8 | 2.06 | 1.32 |
| 10 | 1.96 | 1.41 |
| 24 | 1.83 | 0.94 |
| 30 | 2.73 | 0.96 |
| 48 | 2.63 | 1.87 |
| 54 | 2.86 | 1.56 |

TABLE 6

Mean concentration of calcium in dairy cow blood serum samples

| Time (hrs) | Test Animals (n = 5) | Control Animals (n = 3) |
| --- | --- | --- |
| 0 | 8.14 | 7.59 |
| 2 | 8.43 | 7.19 |
| 4 | 7.57 | 7.55 |
| 6 | 7.27 | 7.77 |
| 8 | 7.55 | 7.65 |
| 10 | 8.21 | 8.35 |
| 24 | 7.38 | 7.72 |
| 30 | 7.27 | 8.03 |
| 48 | 8.89 | 8.66 |
| 54 | 8.76 | 8.41 |

TABLE 7

Mean concentration of magnesium in dairy cow blood serum samples

| Time (hrs) | Test Animals (n = 5) | Control Animals (n = 3) |
| --- | --- | --- |
| 0 | 2.60 | 2.73 |
| 2 | 2.62 | 2.42 |
| 4 | 2.51 | 2.88 |
| 6 | 2.60 | 2.77 |
| 8 | 2.91 | 3.03 |
| 10 | 2.74 | 2.25 |
| 24 | 2.72 | 2.96 |
| 30 | 2.47 | 2.68 |
| 48 | 2.25 | 2.77 |
| 54 | 2.60 | 2.73 |

As shown above in Tables 2 and 5, 5 of the 8 dairy cattle were hypophosphatemic, having an initial phosphate blood serum concentration of less than 1.47 mmol/L. However, upon administration of the bolus compositions, the phosphate levels of the test animals returned to normal levels. For greater clarity, the results included in Table 5 are shown in chart form in FIG. 1, wherein the solid line represents the mean blood phosphate concentration of the test animals, the dashed line represents the mean blood phosphate concentration of the control animals, the dotted line indicates the cut-off for hypophosphatemia (1.47 mmol/L, as discussed above), and the arrows identify times when the bolus compositions were administered to the test animals. Thus, it is clear that the bolus compositions of the present disclosure are capable of treating hypophosphatemia in cattle.

Further, as shown in Tables 3, 4, 6, and 7, the calcium and magnesium blood serum concentrations in test animals were largely unaffected. Thus, it is also clear that the bolus compositions of the present disclosure are capable of treating hypophostatemia in cattle without affecting the concentrations of other minerals and nutrients present in their blood.

It will also be appreciated that, while the above studies were conducted on dairy cattle, the findings are applicable to different types of ruminants including other types of cows such as beef cows, sheep, goats, deer, and the like.

Example 4: Treatment of Post-Partum Dairy Cattle Diagnosed with Subclinical or Clinical Ketosis Using Bolus Compositions of the Present Disclosure Cattle diagnosed with subclinical ketosis (SCK; a blood ketone level of between to 1.4 mmol/L and 3.0 mmol/L) or clinical ketosis (CK; a blood ketone level of greater than 3.0 mmol/L) were used for the study. In total, 24 cattle were examined, 13 of which were used as test animals that received bolus compositions of the present disclosure and 11 of which were used as control animals that did not receive bolus compositions.

The test animals received 2 bolus compositions prepared using the method described in Example 1 immediately following the diagnosis of SCK or CK and two bolus compositions per day for the following two days. The control subjects did not receive any bolus compositions. Blood samples were collected from the cattle before the test animals received treatment (day 0), and 1 day, 2 days, and 3 days thereafter.

The blood serum content of phosphate, calcium, magnesium, and beta-hydroxybutyrate (BHB) was monitored as well as the production and the rumination rates of the cattle.

Blood samples taken from the cattle were centrifuged to separate the serum therefrom and the serum was analyzed for phosphate, calcium, and magnesium content using QUANTICROM® DICA-500, DIMG-250, DIPI-500 assay kits, respectively (QUANTICHROM is a registered trademark of BioAssay Systems LLC, Haywood, CA, USA). The serum extracted from the blood samples was also analyzed for BHB using Freestyle assay kits. The results from these tests are show in FIGS. 2 and 3.

FIG. 2A shows the mean change in phosphate, magnesium, and calcium levels in the test animals over time as compared to the initial serum concentrations of each ion at day 0. In FIG. 2A, line 10a represents the mean change in phosphate, line 12a represents the mean change in magnesium, and the line 14a represents the mean change in calcium in the serum of the test animals.

FIG. 2B shows the mean change in phosphate, magnesium, and calcium levels in the control animals over time as compared the initial serum concentrations of each ion at day 0. In FIG. 2B, line 10b represents the mean change in phosphate, line 12b represents the mean change in magnesium, and the line 14b represents the mean change in calcium in the blood serum of the control animals.

As will be appreciated from FIGS. 2A and 2B, cattle that are suffering from SCK and CK are generally hypophosphatemic. The bolus compositions of the present disclosure increase the mean blood phosphate content of cattle suffering from SCK and CK without affecting the magnesium and calcium content. Notably, as shown in FIG. 2B, the cattle that were not treated with the bolus compositions of the present disclosure experienced a decrease in phosphate serum content, which indicates that the animals were becoming more hypophosphatemic over time.

Figure 3:
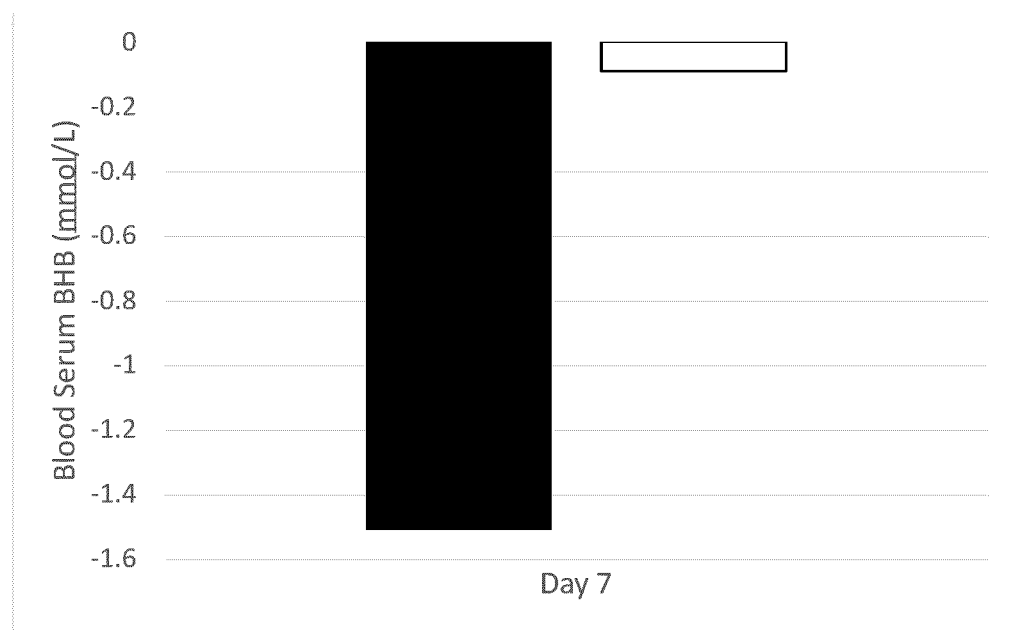
FIG. 3 is a chart showing the mean difference in beta-hydroxybutyrate content 7 days after initial diagnosis of subclinical ketosis or clinical ketosis in dairy cattle treated with bolus compositions of the present disclosure and dairy cattle not treated with the bolus compositions.

Turning now to FIG. 3, there is a chart showing the mean difference in BHB content on day 7 after the initial diagnosis of SCK or CK (day 0) in the test and control animals. As will be appreciated by those of ordinary skill in the art, when an animal enters ketosis, the liver metabolizes fatty acids to provide an energy source for the animal. When the fatty acids are metabolized, ketones including acetone, acetoacetate, and BHB are produced. BHB is generally the most stable of the ketones produced by fatty acid metabolism and thus is often used as an indicator for ketosis. In that regard, a blood serum BHB content of greater than 1.4 mmol/L indicates that a cow may have SCK, while a blood serum BHB content of greater than 3 mmol/L indicates that a cow may have CK. In FIG. 3, the black bar represents the mean change in blood serum BHB content in test animals, while the white bar represents the mean change in blood serum BHB content of the control animals.

From FIG. 3 it is clear that the bolus compositions of the present disclosure are capable of significantly reducing the BHB serum content in cattle suffering from SCK or clinical ketosis, which, in turn, indicates an improvement in the metabolic health of the cattle, as the level of ketosis of the cattle may become less severe.

Figure 4:
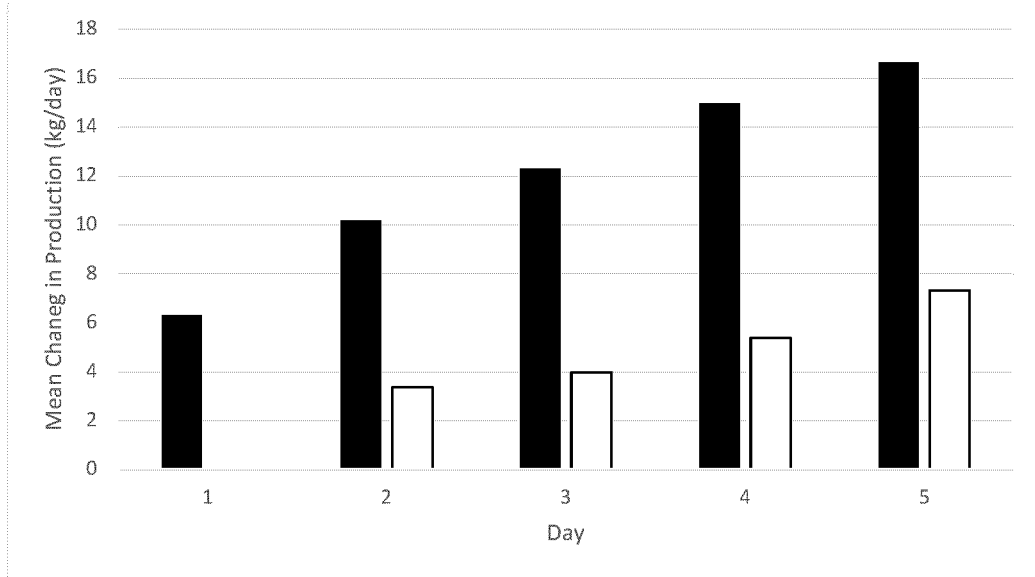
FIG. 4 is a chart showing the mean change in production over time in dairy cattle diagnosed with clinical ketosis that were treated with bolus compositions of the present disclosure and that were not treated with the bolus compositions as compared to their production on the day of diagnosis.

Referring now to FIG. 4, there is shown a chart illustrating the mean change in production of the test animals (black bars) and control animals (white bars) diagnosed with CK as compared to their production on the day they were diagnosed with CK. It is noted that production refers to the amount of milk produced in kg per day.

In more detail, there was a significant difference in production between the test and control subjects diagnosed with CK. As shown in FIG. 4, cattle treated with the bolus compositions of the present disclosure were able to produce milk one day after initial diagnosis, whereas the cattle that were not treated where not able to produce milk until the second day. As well, it is noted that it took the control animals 5 days to reach the same level of production that the test animals reached on day 1.

Figure 5:
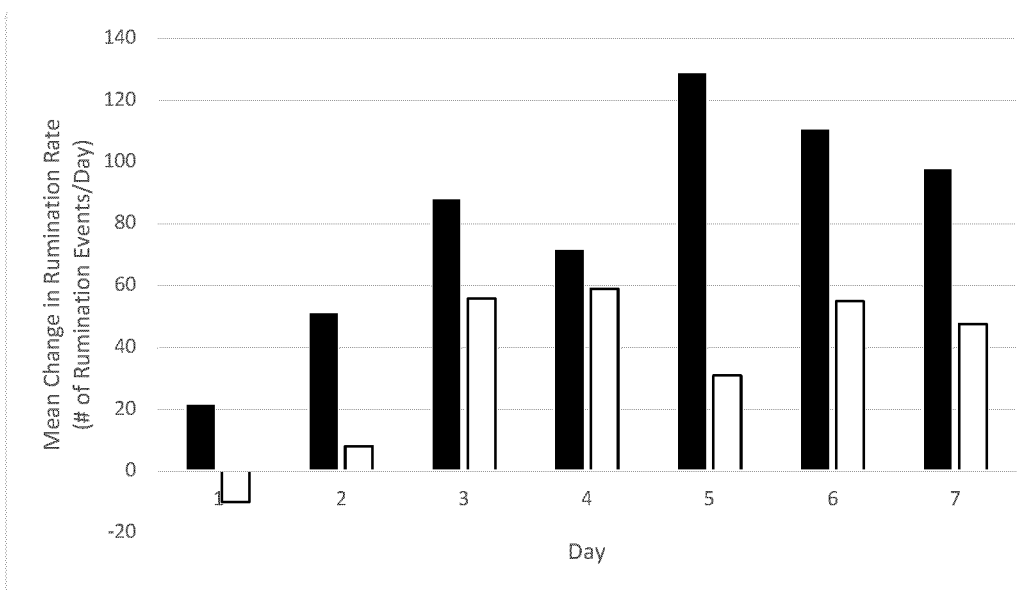
FIG. 5 is a chart showing the mean change in rumination rate over time of dairy cattle diagnosed with subclinical ketosis that were treated with the bolus compositions of the present disclosure and that were not treated with the bolus compositions as compared to their rumination rate on the day of diagnosis.

Referring now to FIG. 5, there is shown a chart illustrating the mean change in rumination rate of the test animals (black bars) and control animals (white bars) diagnosed with SCK over time as compared to their rumination rate on the day that they were diagnosed (day 0). As used herein, "rumination rate" refers to the number of rumination events that occur over the course of a day, wherein "rumination events" refer to when ruminants such as cows regurgitate previously consumed food to chew it further. In this experiment, the rumination rate was determined using a rumination monitor provided by Allflex (Saint-Hyacinthe, Quebec, Canada).

FIG. 5 shows that there was a significant difference in the mean change rumination rate between the test and control subjects diagnosed with SCK. In more detail, the test animals diagnosed with SCK experienced significantly more rumination events per day than the control animals. The test animals diagnosed with SCK were therefore eating more the control animals, which indicates that any anorexia that the cattle may have been suffering from was at least partially ameliorated.

Thus, the bolus compositions of the present disclosure may provide a number of benefits to ruminants such as cattle that are experiencing SCK or CK including, for example, the amelioration of hypophosphatemia, decreased production, and decreased rumination or anorexia. Further, as indicated above by the change in blood serum BHB levels in the cattle treated with the bolus compositions of the present disclosure, the bolus compositions may also treat SCK or CK in ruminants.

The invention claimed is:

1. A solid bolus composition for the prevention or treatment of hypokalemia and hypophosphatemia in a ruminant, the solid bolus composition comprising:
   70 wt % to 80 wt % potassium phosphate dibasic; and
   20 wt % to 30 wt % water.

2. The solid bolus composition of claim 1, wherein the solid bolus composition is coated with a coating.

3. The solid bolus composition of claim 2, wherein the coating is a lipid-based coating.

4. The solid bolus composition of claim 2, wherein the coating comprises an acetylated triglyceride.

5. The solid bolus composition of claim 2, wherein the coating is present in an amount of about 1 g to about 10 g.

6. The solid bolus composition of claim 1, wherein the weight ratio of potassium phosphate dibasic to water in the solid bolus composition is 80:20.

7. The solid bolus composition of claim 1, further comprising a source of calcium, selenium, sodium, zinc, iodine, chloride, choline, copper or any combination thereof.

8. The solid bolus composition of claim 1, further comprising vitamin A, vitamin D, vitamin E, or any combination thereof.

9. The solid bolus composition of claim 1, wherein a wick is inserted within the solid bolus composition.

10. The solid bolus composition of claim 9, wherein the wick is degradable, dissolvable, or decomposable in the rumen of the ruminant.

11. The solid bolus composition of claim 10, wherein the wick comprises cellulose or a cellulosic material.

12. The solid bolus composition of claim 1, wherein a weight of the solid bolus composition is in a range of about 50 g to about 250 g.

13. The solid bolus composition of claim 1, wherein the shape of the solid bolus composition is spherical, cylindrical, capsular, torpedo-shaped or donut-shaped.

* * * * *